United States Patent
Kobayakawa et al.

(10) Patent No.: US 6,823,715 B2
(45) Date of Patent: Nov. 30, 2004

(54) GAS CONCENTRATION MEASURING APPARATUS AND METHOD

(75) Inventors: Tatsu Kobayakawa, Ibaraki-ken (JP); Hiroshi Yamada, Ibaraki-ken (JP); Hideki Toda, Ibaraki-ken (JP); Sachiko Saitou, Ibaraki-ken (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/391,016

(22) Filed: Mar. 19, 2003

(65) Prior Publication Data

US 2004/0065139 A1 Apr. 8, 2004

(30) Foreign Application Priority Data

Mar. 22, 2002 (JP) ........................................ 2002-080676

(51) Int. Cl.[7] .............................................. G01N 29/02
(52) U.S. Cl. ........................ 73/24.06; 73/24.01; 73/597; 73/602
(58) Field of Search ............................... 73/23.2, 24.01, 73/24.06, 597, 598, 602

(56) References Cited

U.S. PATENT DOCUMENTS 3,981,176 A * 9/1976 Jacobs ........................ 73/24.01
5,313,820 A * 5/1994 Aylsworth .................. 73/24.01

* cited by examiner

*Primary Examiner*—Daniel S. Larkin
(74) *Attorney, Agent, or Firm*—Sughrue Mion, PLLC

(57) ABSTRACT

A gas-concentration measuring apparatus for measuring the concentration variation of gas residing in a target region. The gas-concentration measuring apparatus comprises an ultrasound-transmitter adapted to transmit an ultrasound in response to an ultrasound-generating signal having a rate of voltage change equal to or greater than a slew rate of an operational amplifier, and further adapted to output the ultrasound-generating signal. An ultrasound-receiver adapted to receive the ultrasound wave passed through the gas residing in the target region, and further adapted to convert the received ultrasound into an electrical signal serving as a received ultrasound signal is provided. A gas-concentration determiner adapted to input the ultrasound-generating signal and the received ultrasound wave signal into the operational amplifier to generate an amplified transmitting-side chopping wave and an amplified receiving-side chopping wave is further provided. The gas-concentration determiner is further adapted to compare the transmitting-side and receiving-side chopping waves independently with corresponding given threshold voltages to detect a first pair of time points when the respective chopping waves become equal to or greater than the corresponding given threshold voltages or to detect a second pair of time points when the respective chopping waves become equal to or less than the corresponding given threshold voltages. The gas-concentration determiner is further adapted to determine the concentration variation in the gas based on the pair of time points.

10 Claims, 7 Drawing Sheets

GAS CONCENTRATION MEASURING APPARATUS AND METHOD

FIELD OF THE DISCLOSURE

This disclosure teaches techniques related to measurement of gas-concentration. Specifically, the teachings deal with measuring the variation in concentration gas residing in a target region.

BACKGROUND

Several conventional techniques have been developed for measurement of variations in gas concentration variation or gas flow-rate. These techniques include a dielectric relaxation method for measuring the dielectric constant of a substance, an absorption spectrum method for measuring the absorption distribution of electromagnetic waves, and an ultrasonic attenuation measuring method for measuring the amplitude decrement in ultrasounds after propagation. However, these techniques are generally insufficient at least in terms of time resolution.

A propagation-time-difference method is a conventional technique for measuring an acoustic propagation time between a transmitter and a receiver. This technique is simple and has a potential for achieving enhanced time resolution. In this technique, a standing wave is transmitted from a transmitter to a receiver. A propagation time is determined from a phase difference (phase shift) between the original standing wave in the transmitter and the received signal from the receiver. The variation in concentration or flow-rate of gas residing between the transmitter and the receiver is measured based on the propagation time.

For determining the above phase difference, signal processing on the side of the receiver is necessary to detect a time point when the amplitude of the received signal becomes greater than a given threshold. This is needed to determine a zero-cross point. However, the time point needs to be arranged to conform with the peak amplitude level of the received signal corresponding to that of the original standing wave. In addition, the amplitude of the received signal itself is undesirably fluctuated due to other physical factors, such as the temperature or humidity of the gas. This results in a large dispersion in the zero-cross points and the measured phase differences. This problem is referred to as "zero-cross problem" herein.

In order to avoid the zero-cross problem, alternative methods have been conventionally proposed. These alternate methods includes a sing around method in which a received signal is returned to a transmitting end. The cycle of the returned signal is determined to determine the velocity of sonic wave. In a further alternate method, secondary/tertiary reflected waves between transmitting and receiving sections are detected to determine the velocity of sonic waves in a stable manner. In these methods, the variation in the concentration or flow rate of gas residing between the transmitting and receiving sections can be measured based on the determined sonic-wave velocity. These methods are free from the zero-cross problem because there is no need for determining the time point when the amplitude of a received signal becomes greater than a given threshold.

The sing around method or the sonic-wave velocity measuring method can provide a solution to the zero-cross problem. However, these methods take a substantial amount of time to complete their measurement over the entire period of the reflection time of sonic waves. This prevents the measurement of the variation in gas concentration in real time with a high time resolution.

The disclosed teachings are aimed at overcoming some of the above noted disadvantages.

SUMMARY

To realize the advantages of the disclosed teachings there is provided a gas-concentration measuring apparatus for measuring the concentration variation of gas residing in a target region The gas-concentration measuring apparatus comprises an ultrasound-transmitter adapted to transmit an ultrasound in response to an ultrasound-generating signal having a rate of voltage change equal to or greater than a slew rate of an operational amplifier, and further adapted to output the ultrasound-generating signal. An ultrasound-receiver adapted to receive the ultrasound wave passed through the gas residing in the target region, and further adapted to convert the received ultrasound wave into an electrical signal serving as a received ultrasound signal is provided. A gas-concentration determiner adapted to input the ultrasound-generating signal and the received ultrasound signal into the operational amplifier to generate an amplified transmitting-side chopping wave and an amplified receiving-side chopping wave is further provided. The gas-concentration determiner is further adapted to compare the transmitting-side and receiving-side chopping waves independently with corresponding given threshold voltages to detect a first pair of time points when the respective chopping waves become equal to or greater than the corresponding given threshold voltages or to detect a second pair of time points when the respective chopping waves become equal to or less than the corresponding given threshold voltages. The gas-concentration determiner is further adapted to determine the concentration variation in the gas based on the pair of time points.

Another aspect of the disclosed teachings is a gas-concentration measuring method for measuring the concentration variation in gas residing in a target region. The gas-concentration measuring method comprises transmitting an ultrasound wave in response to an ultrasound-generating signal having a voltage change equal to or greater than a slew rate of an operational amplifier. The ultrasound wave passed through the gas residing in the target region is converted into an electrical signal serving as a received ultrasound signal. The ultrasound-generating signal and the received ultrasound signal are amplified to generate a transmitting-side chopping wave and an amplified receiving-side chopping wave. The transmitting-side and receiving-side chopping waves are compared independently with corresponding given threshold voltages to detect a first pair of time points when the respective chopping waves become equal to or greater than the corresponding given threshold voltages or a second pair of time points when the respective chopping waves become equal to or less than the corresponding given threshold voltages. The concentration variation in the gas is determined in accordance with the first and second pairs of time points.

BRIEF DESCRIPTION OF THE DRAWINGS

The above objectives and advantages of the present invention will become more apparent by describing in detail preferred embodiments thereof with reference to the attached drawings in which.

DETAILED DESCRIPTION

Figure 1:
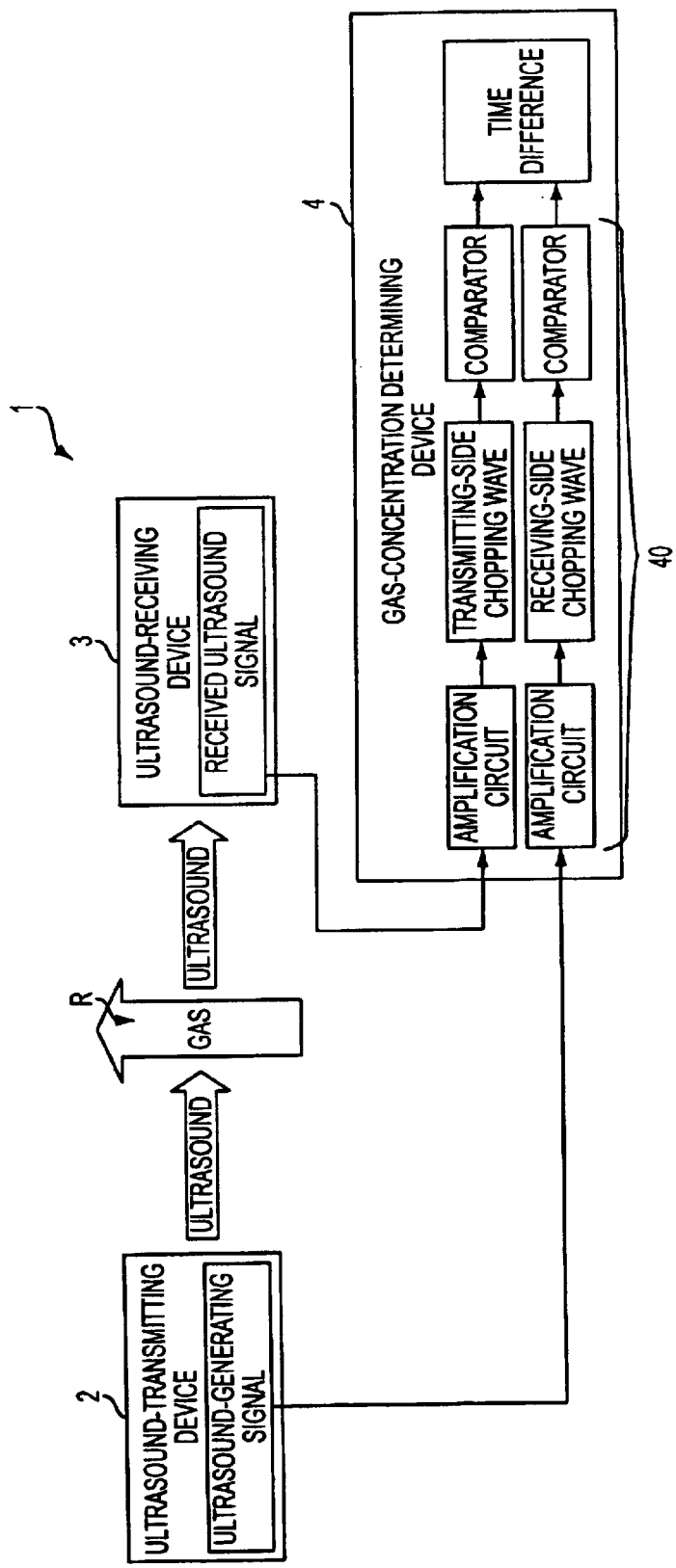
FIG. 1 is a schematic block diagram of one example of a gas-concentration measuring apparatus embodying the disclosed teachings.

With reference to drawings, an example embodying the disclosed teachings is described in detail. FIG. 1 is a schematic block diagram of such an example of a gas-concentration measuring apparatus. The gas-concentration measuring apparatus 1 measures the concentration variation of gas residing in a target region R. The gas-concentration measuring apparatus 1 comprises an ultrasound-transmitting device 2, an ultrasound-receiving device 3, and a gas-concentration determining device 4. The ultrasound-transmitting device 2 is operable to transmit an ultrasound in response to an ultrasound-generating signal having a voltage change equal to or greater than the slew rate of an operational amplifier. The ultrasound-transmitting device 2 is operable to output the ultrasound-generating signal. The ultrasound-receiving device 3 is operable to receive the ultrasound passed through the gas residing in the target region R. It then converts the received ultrasound into an electrical signal serving as a received ultrasound signal. The gas-concentration determining device 4 is operable to input the ultrasound-generating signal and the received ultrasound signal into the operational amplifier to generate an amplified transmitting-side chopping wave and an amplified receiving-side chopping wave. It is further operable to compare the transmitting-side and receiving-side chopping waves independently with corresponding given threshold voltages to detect a pair of first time points when the respective copping waves become equal to or greater than the corresponding given threshold voltages. It is also operable to detect a pair of second time points when the respective copping waves become equal to or less than the corresponding given threshold voltages. It can determine the variation in concentration of the gas based on the pair of time points.

The term "slew rate", referred to herein, is an index representing a maximum response speed of the above operational amplifier. More specifically, the slew rate refers to a change in the output voltage of the operational amplifier to be observed by an oscilloscope when an optimal pulse or input voltage having a high rise-rate is input to the operational amplifier. The slew rate is generally represented by V/$\mu$s, which means maximum voltage per $\mu$s at the rising or falling edge of an output pulse from the operational amplifier.

The above gas-concentration measuring apparatus 1 will be described in more detail with reference to FIGS. 2 to 7.

Figure 2:
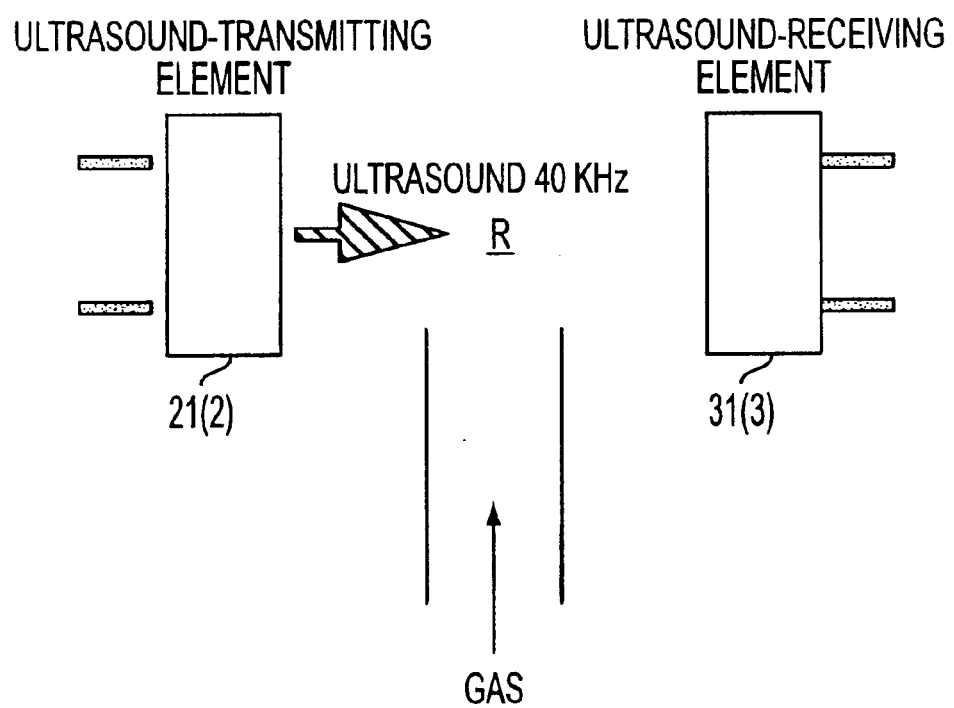
FIG. 2 is a schematic block diagram showing an example of a part of the gas-concentration measuring apparatus around a target region.
Figure 3:
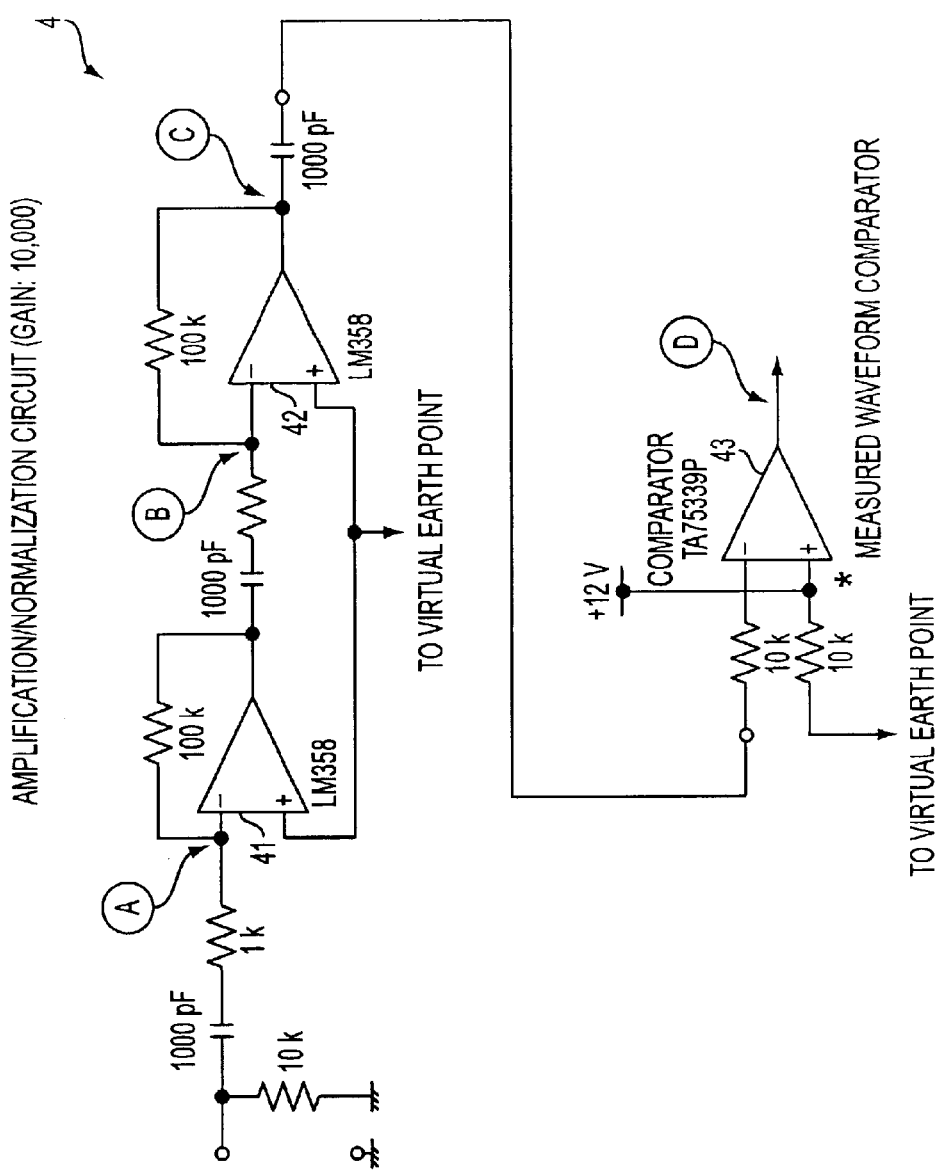
FIG. 3 is a block diagram showing an example of a gas-concentration determining device of the gas-concentration measuring apparatus.
Figure 4:
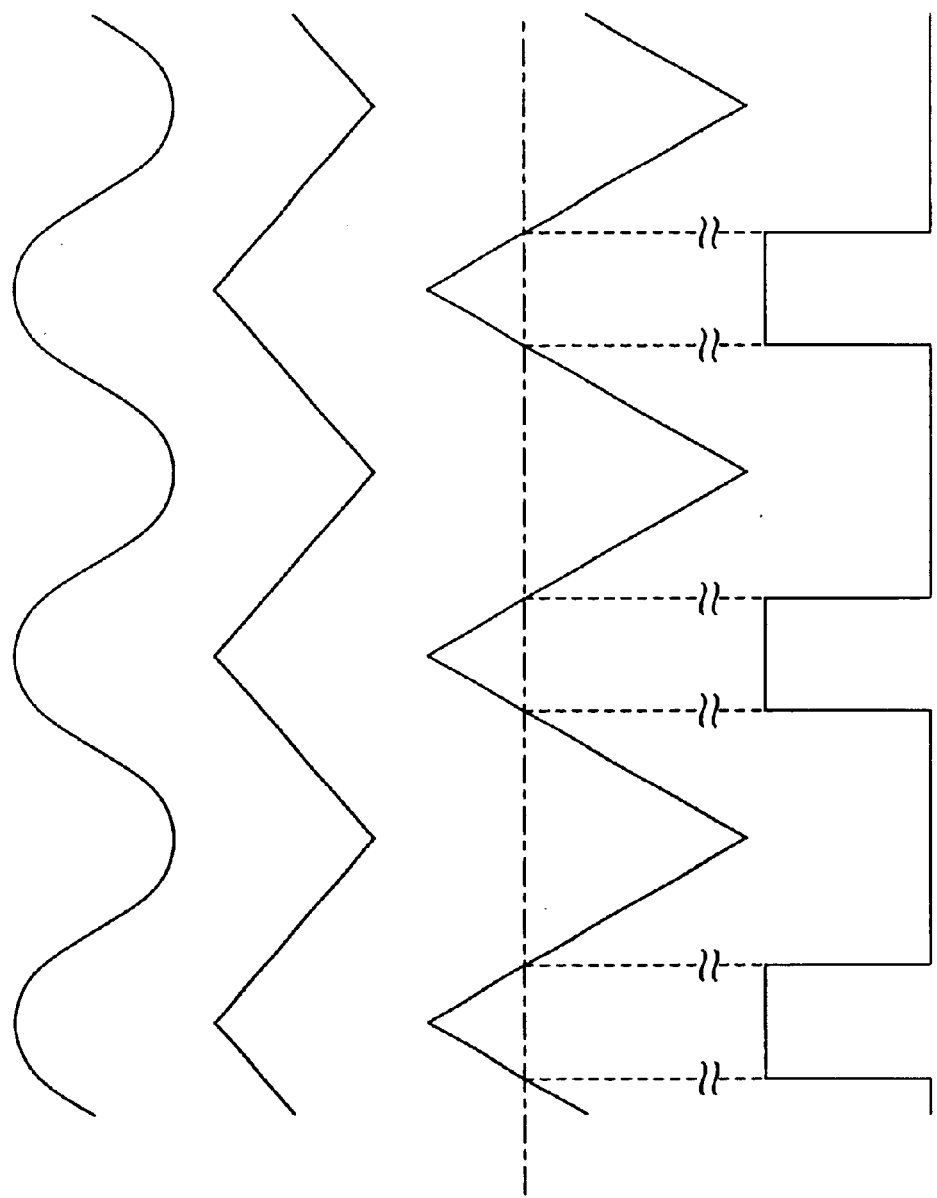
FIGS. 4A, 4B, 4C and 4D are waveform charts of signals in the respective sections of the gas-concentration determining device in FIG. 3.
Figure 5:
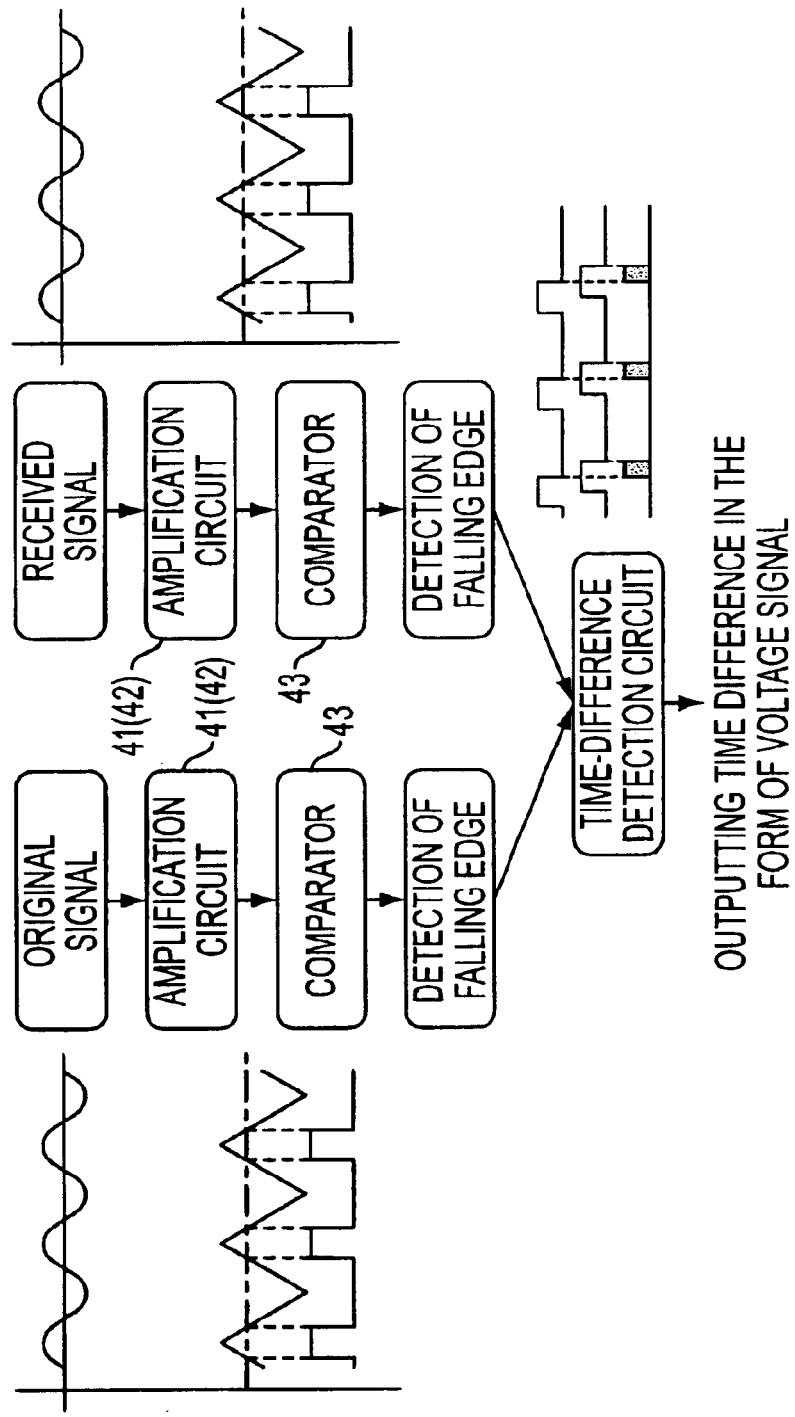
FIG. 5 is an explanatory diagram of a processing executed by the gas-concentration determining device.

FIG. 2 shows a part of the gas-concentration measuring apparatus 1 around a target region R. FIG. 3 shows the gas-concentration determining device 4. FIGS. 4A, 4B, 4C and 4D shows signal waveform in the respective sections of the gas-concentration determining device 4 in FIG. 3. FIG. 5 shows a processing executed by the gas-concentration determining device 4.

As shown in FIG. 2, the ultrasound-transmitting device 2 and the ultrasound-receiving device 3 include an ultrasound-transmitting element 21 and an ultrasound-receiving element 31, respectively. For example, each of the elements 21, 31 may be comprised of a piezoelectric element. The ultrasound-transmitting element 21 is operable to transmit an ultrasound, for example, having a frequency of 40 KHz, in response to the ultrasound-generating signal. In the target region air and carbon dioxide are passed by turns. After passing through the target region, the transmitted ultrasound is received by the ultrasound-receiving element 3. The received ultrasound is then converted into an electrical signal serving as the received ultrasound signal by the ultrasound-transmitting device 2. The received ultrasound signal is then output.

As shown in FIG. 3, the gas-concentration determining device 4 includes a pair of amplification/normalization circuits 40 each having a gain of about 10,000. As shown in FIG. 3, each of the amplification/normalization circuit 40 includes first and second operational amplifiers 41, 42, and a comparator 43. The pair of amplification/normalization circuits 40 are provided for the ultrasound-generating signal and the received ultrasound signal, respectively. The ultrasound-generating signal to be input to one of the amplification/normalization circuits 40 is arranged in advance to have a voltage change equal to or greater than the slew rate (e.g. 0.1 V/$\mu$s) of the first operational amplifier 41.

Signals at the points A, B, C and D of the amplification/normalization circuit 40 are shown in FIGS. 4A, 4B, 4C and 4D, respectively. The ultrasound-generating signal and the received ultrasound signal in the form of a sine curve as shown in FIG. 4A, are input to the corresponding first operational amplifiers 41, respectively.

Since the ultrasound-generating signal is arranged in advance to have a voltage change equal to or greater than the slew rate (e.g. 0.1 V/$\mu$s) of the first operational amplifier 41, an output signal of the first operational amplifier 41 will have a voltage change in conformity with the slew rate. More specifically, the sine curve of the entered ultrasound-generating signal is amplified by the first operational amplifier 41 under the restriction of the slew rate thereof, and formed as a chopping wave serving as the transmitting-side chopping wave as shown in FIG. 4B. In the same manner, the received ultrasound signal is formed as the receiving-side chopping wave. It is understood that each of these chopping waves has the same frequency of the corresponding input signal. That is, regardless of the amplitude of the input sine curve, a chopping wave will be generated from the first operational amplifier with the same frequency as that of the input sine curve. Because of this function, the sine curve having a widely varying amplitude due to physical conditions other than the gas concentration can still be normalized to a constant chopping wave.

These chopping waves (the transmitting-side and receiving-side chopping waves) are further amplified by the corresponding second amplifiers 42, respectively, as shown in FIG. 4C. The amplified chopping waves are compared with the given threshold voltages of the corresponding comparators 43 to detect the pair of first time points when the respective copping waves become equal to or greater than the corresponding given threshold voltages. Likewise, the pair of second time points are detected when the respective copping waves become equal to or less than the corresponding given threshold voltages. Each of the chopping waves is formed as a rectangular wave having a rising edge at the first time point and a falling edge at the second time point, as shown in FIG. 4D.

As described above, both the ultrasound-generating signal and the received ultrasound signal are entered into the gas-concentration determining device 4. As shown in the left flow chart of FIG. 5, the ultrasound-generating is amplified and formed as the transmitting-side chopping wave through the first operational amplifier 41 (amplification circuit). The transmitting-side chopping signal is then compared with the given threshold voltage and formed as the rectangular wave through the comparator 43. Then, the second time point at the falling edge of the rectangular wave is detected.

Simultaneously, the received ultrasound signal is subjected to a processing similar to the ultrasound-generating signal as shown in right flow chart of FIG. 5. That is, the received ultrasound signal is amplified and formed as the receiving-side chopping wave through the first operational amplifier 41 (amplification circuit). The receiving-side chopping signal is then compared with the given threshold voltage and formed as the rectangular wave through the comparator 43. Then, the second time point at the falling edge of the rectangular wave is detected.

Then, the gas-concentration determining device 4 determines the time difference between the respective detected second time points at the falling edges of the rectangular waves originated from the ultrasound-generating signal and the received ultrasound signal. It then outputs the determined time difference in the form of a voltage signal. This time difference corresponds to the phase difference between the ultrasound-generating signal and the received ultrasound signal. It further corresponds to the variation in concentration of the gas residing in the target region R through which the transmitted ultrasound wave has passed.

While the above described apparatus is configured to detect the time difference between the pair of second time points at the falling edges of the rectangular waves, the time difference between the pair of first time points at the rising edges of the rectangular waves may also be detected.

An actual measurement result will be described with reference to FIGS. 6 and 7.

Figure 6:
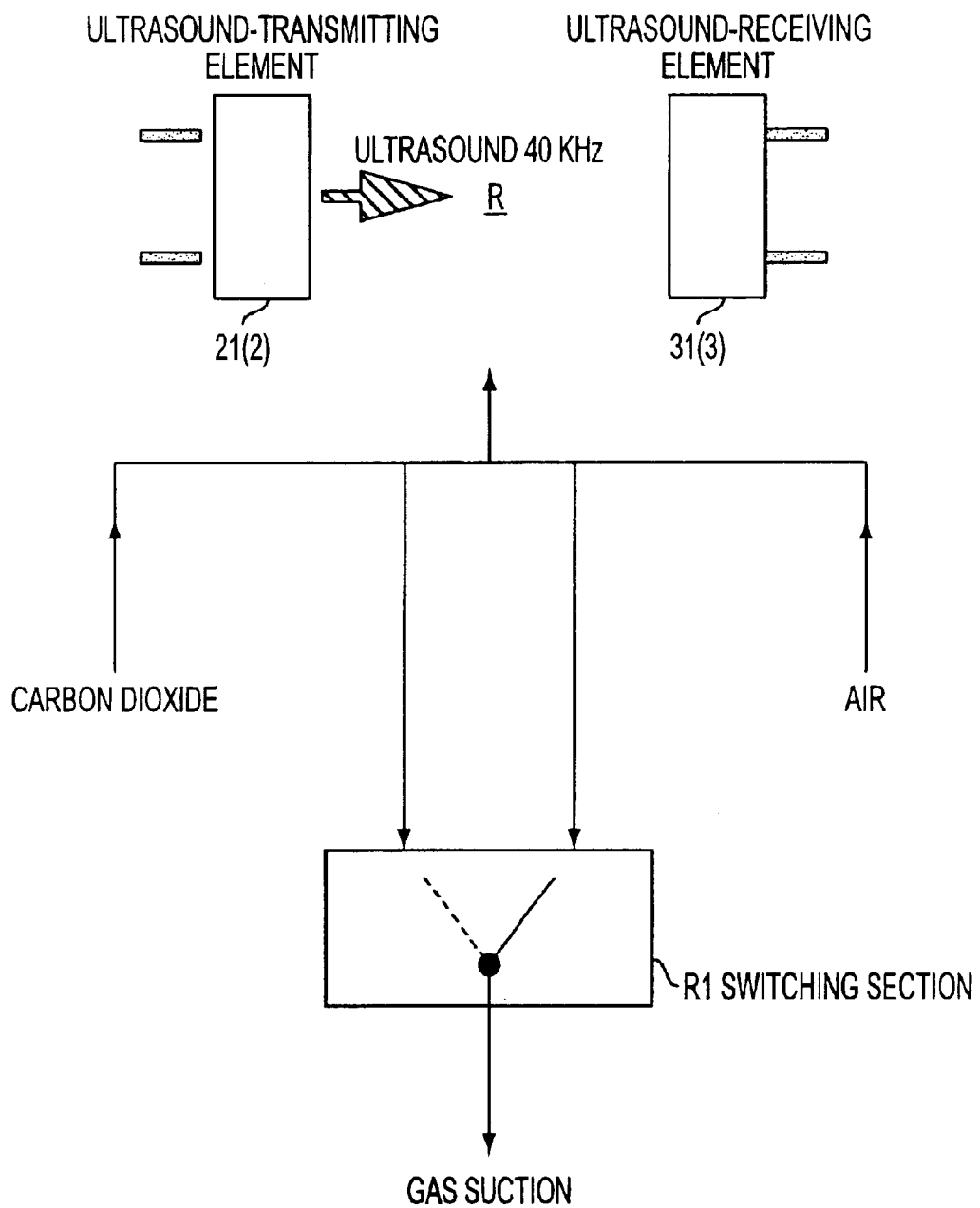
FIG. 6 is a schematic block diagram showing an example of a gas-switching device.
Figure 7:
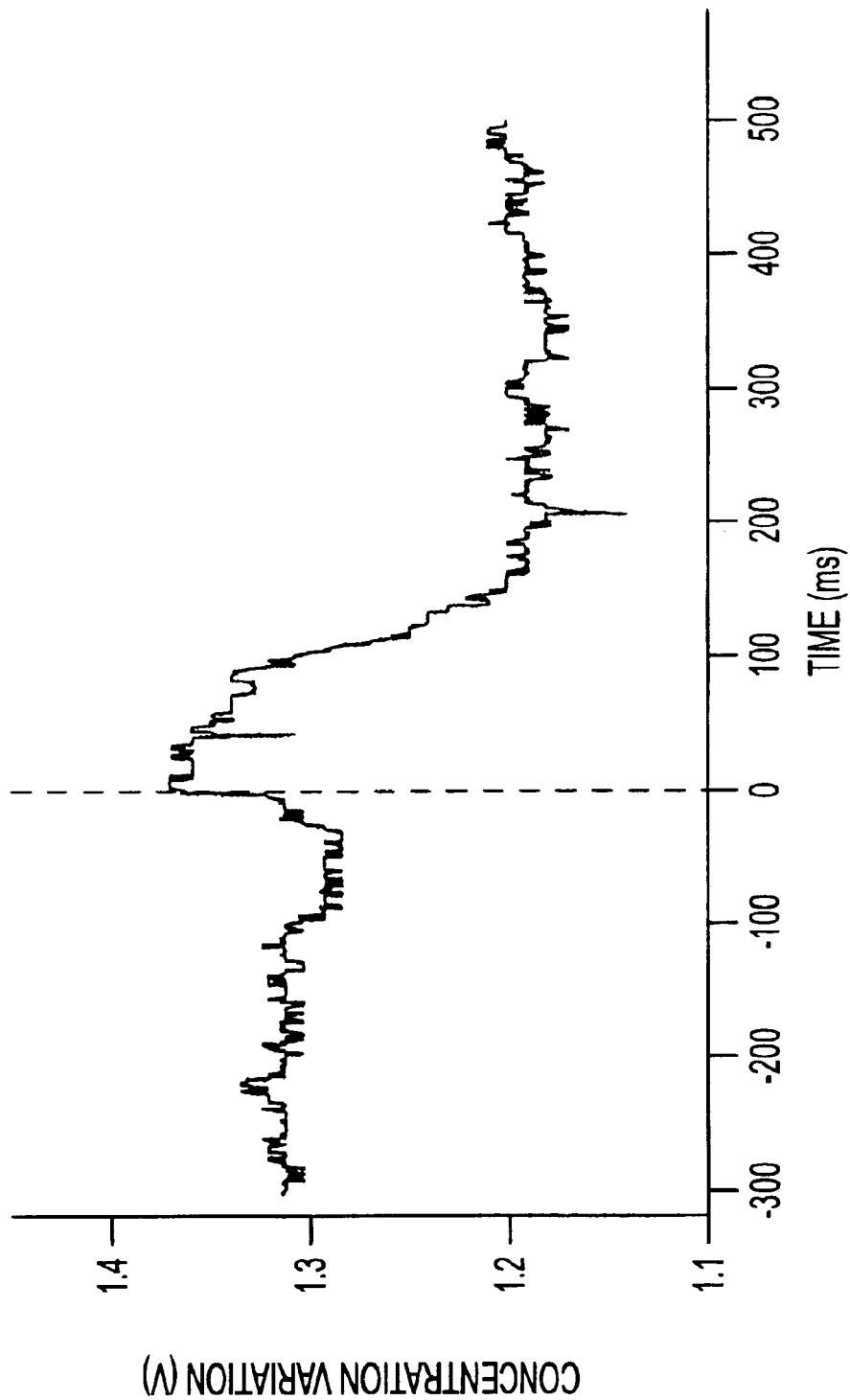
FIG. 7 is a diagram showing a result from a measurement using the gas-concentration measuring apparatus under a gas switching operation according to the gas-switching device in FIG. 6.

FIG. 6 shows a gas-switching device, and FIG. 7 shows a result from a measurement using the gas-concentration measuring apparatus under a gas switching operation according to the gas-switching device in FIG. 6.

In FIG. 6, both carbon dioxide gas and air can be continuously supplied to the target region R. For example, if a switching section RI is brought into fluid communication with air to suck the air through the switching section RI, only the carbon dioxide gas will be supplied to the target region R. Then, the gas-concentration measuring apparatus 1 transmits an ultrasound from the ultrasound-transmitting element 21 to pass the ultrasound through the gas in the target region R so as to measure the variation in concentration of the gas.

In this measurement, the carbon dioxide gas is first passed through the switching section R1 to supply only the air to the target region R. Then the switching section R1 is switched by a solenoid valve to suck the air and supply only the carbon dioxide. By such an operation, the variation in concentration of the gas before-and-after the switching operation is measured.

FIG. 7 is a result obtained by repeating the above measurement thirty times, and weighted-averaging the measurement values on the basis of the time just before the solenoid valve is switched. In this manner, measurement data could be obtained with a high S/N ratio without any random noise.

FIG. 7 shows that the switching operation of switching the air to the carbon dioxide gas was initiated at the time 0, the replacement of the air with the carbon dioxide gas being initiated after 100 ms, and after more about 100 ms or 200 ms from the solenoid-valve switching operation, the replacement of the air with the carbon dioxide gas being completed.

The shift of the voltage signal (concentration variation) at the time 0 is caused by the driving voltage of the solenoid valve.

In the above example embodying the present invention, an ultrasound wave is transmitted in response to the ultrasound-generating signal having a voltage change equal to or greater than the slew rate of the operational amplifier. The variation in concentration of gas residing in a target region is determined based on the ultrasound-generating signal and the received ultrasound signal obtained from the ultrasound passed through the gas. Thus, the variation in concentration of the gas can be measured highly accurately without the zero-cross problem and in real time with a high time resolution.

Further, the concentration variation can be measured with a high level of accuracy within milliseconds. Thus, in addition to the variation in gas-concentration, the variation in gas mixing ratio can be measured in real time. The high time resolution that is achieved makes it possible to determine if a mixed gas is homogeneously mixed, or any turbulence is generated therein. That is, if the mixed gas is not homogeneously mixed or any turbulence is generated therein, the velocity of sonic waves will be largely dispersed in a target region. Thus, these states can be measured in accordance with the dispersion of obtained data.

The above gas-concentration measuring technique with a high time resolution makes it possible to facilitate constructing chemical plants capable of controlling gases with higher accuracy. It can also be used for developing engines with enhanced power.

Using the disclosed techniques, the variation in concentration of gas residing in a target region can be measured without the zero-cross problem and in real time. This is done by transmitting an ultrasound in response to the ultrasound-generating signal having a voltage change equal to or greater than the slew rate of the operational amplifier, and determining the variation in concentration of the gas based on the ultrasound-generating signal and the received ultrasound signal obtained from the ultrasound passed through the gas. This technique can be applied to not only a gas-concentration measuring apparatuses, but also a gas flow-rate measuring apparatus for measuring the flow-rate variation of gas in a target region.

While the above embodiment has been explained in conjunction with a case where air and carbon dioxide gas or air and nitrogen gas are supplied by turns to the target region, the gas to be supplied to the target region is not limited to such gases, but any other suitable gas combination may be used.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A gas-concentration measuring apparatus for measuring the concentration variation of gas residing in a target region, said gas-concentration measuring apparatus comprising:

an ultrasound-transmitter adapted to transmit an ultrasound wave in response to an ultrasound-generating signal having a rate of voltage change equal to or greater than a slew rate of an operational amplifier, said ultrasound wave being transmitted through the gas residing in the target region;

an ultrasound-receiver adapted to receive the ultrasound wave after passing through said gas residing in said target region, and further adapted to convert said received ultrasound wave into an electrical signal serving as a received ultrasound signal; and a gas-concentration determiner adapted to input said ultrasound-generating signal and said received ultrasound signal into said operational amplifier to generate an amplified transmitting-side chopping wave and an amplified receiving-side chopping waver;

wherein the gas-concentration determiner is further adapted to compare said transmitting-side and receiving-side chopping waves independently with corresponding given threshold voltages to detect a first pair of time points when said respective chopping waves become equal to or greater than said corresponding given threshold voltages or to detect a second pair of time points when said respective chopping waves become equal to or less than said corresponding given threshold voltages, and wherein the gas-concentration determiner is further adapted to determine the concentration variation in said gas based on said pair of time points.

2. A gas-concentration measuring method for measuring the concentration variation in gas residing in a target region, said gas-concentration measuring method comprising:

transmitting an ultrasound wave in response to an ultrasound-generating signal having a voltage change equal to or greater than a slew rate of an operational amplifier;

passing the ultrasound wave through the gas residing in the target region;

converting the ultrasound wave after passing through said gas residing in said target region into an electrical signal serving as a received ultrasound signal;

amplifying the ultrasound-generating signal and the received ultrasound signal to generate an amplified transmitting-side chopping wave and an amplified receiving-side chopping wave;

comparing said transmitting-side and receiving-side chopping waves independently with corresponding given threshold voltages to detect a first pair of time points when said respective chopping waves become equal to or greater than said corresponding given threshold voltages or a second pair of time points when said respective chopping waves become equal to or less than said corresponding given threshold voltages; and determining the concentration variation in said gas in accordance with said first and second pairs of time points.

3. The apparatus of claim 1, wherein the ultrasound transmitter comprises a piezoelectric element.

4. The apparatus of claim 1, wherein the ultrasound receiver comprises a piezoelectric element.

5. The apparatus of claim 1, wherein the gas-concentration determiner comprises a pair of amplification circuits.

6. The apparatus of claim 5, wherein each of said pair of amplification circuits includes a pair of operational amplifiers.

7. The apparatus of claim 1, wherein the gas-concentration determiner is adapted to determine a time difference between the pair of second time points at falling edges of rectangular waves corresponding to the ultrasound-generating signal and the received ultrasound signal.

8. The apparatus of claim 7, wherein the gas-concentration determiner is adapted to output a time difference corresponding to a phase difference between the ultrasound-generating signal and the received ultrasound signal as voltage signal.

9. The apparatus of claim 1, wherein the gas-concentration determiner is adapted to determine a time difference between the pair of first time points at rising edges of rectangular waves corresponding to the ultrasound-generating signal and the received ultrasound signal.

10. The apparatus of claim 9, wherein the gas-concentration determiner is adapted to output a time difference corresponding to a phase difference between the ultrasound-generating signal and the received ultrasound signal as voltage signal.

* * * * *